United States Patent [19]
Yogev et al.

[11] Patent Number: 5,958,761
[45] Date of Patent: *Sep. 28, 1999

[54] BIOREACTOR AND SYSTEM FOR IMPROVED PRODUCTIVITY OF PHOTOSYNTHETIC ALGAE

[75] Inventors: Amnon Yogev, Rehovot; Dan Yakir, Kiryat Ekron, both of Israel

[73] Assignee: Yeda Research and Developement Co. Ltd., Rehovot, Israel

[ * ] Notice: This patent issued on a continued prosecution application filed under 37 CFR 1.53(d), and is subject to the twenty year patent term provisions of 35 U.S.C. 154(a)(2).

[21] Appl. No.: 08/669,320
[22] PCT Filed: Jan. 10, 1995
[86] PCT No.: PCT/US95/00019
  § 371 Date: Jul. 9, 1996
  § 102(e) Date: Jul. 9, 1996
[87] PCT Pub. No.: WO95/19424
  PCT Pub. Date: Jul. 20, 1995

[30] Foreign Application Priority Data

Jan. 12, 1994 [IL] Israel ......... 108321

[51] Int. Cl.⁶ ............ C12M 1/42; C12N 1/12
[52] U.S. Cl. ......... 435/292.1; 47/1.4; 435/257.1
[58] Field of Search ............ 435/292.1, 257.1, 435/257.3; 47/1.4

[56] References Cited

U.S. PATENT DOCUMENTS

| | | |
|---|---|---|
| 2,715,795 | 8/1955 | Pallotta et al. . |
| 3,303,608 | 2/1967 | Hannan . |
| 3,986,297 | 10/1976 | Ichimura et al. . |
| 4,324,068 | 4/1982 | Anthony . |
| 4,840,905 | 6/1989 | Kearns et al. . |
| 4,889,812 | 12/1989 | Guinn et al. . |
| 4,970,166 | 11/1990 | Mori . |

FOREIGN PATENT DOCUMENTS

| | | | |
|---|---|---|---|
| 2 564 854 | 11/1985 | France | 435/292.1 |
| 2 678 946 | 1/1993 | France | 435/292.1 |
| 58-51888 | 3/1983 | Japan . | |
| 4-287678 | 10/1992 | Japan | 435/292.1 |
| 1521404 | 11/1989 | U.S.S.R. | 435/292.1 |

OTHER PUBLICATIONS

English language translation of JP 4–287678, Jan. 1997.
English language translation of FR 2564854, Jan. 1997.
English Language Abstract of JP 58–51888,(1983).

*Primary Examiner*—William H. Beisner
*Attorney, Agent, or Firm*—Greenblum & Bernstein, P.L.C.

[57] ABSTRACT

A bioreactor for improved productivity of photosynthetic algae includes a tubular housing surrounding a tubular envelope located therein. The housing and envelope define a space therebetween to be filled with fluid. The housing and envelope are made of at least a translucent material and have inlet and outlet ports providing access to the space and the interior of the envelope. A mixer for mixing algae media is disposed inside the envelope. There is also provided a bioreactive system, wherein the envelope contains a fluid of selective refractive index and wherein, for a given geometrical relationship between the housing and the envelope, the radiation concentration power is controlled by modifying the refractive index of the fluid.

22 Claims, 1 Drawing Sheet

BIOREACTOR AND SYSTEM FOR IMPROVED PRODUCTIVITY OF PHOTOSYNTHETIC ALGAE

BACKGROUND OF THE INVENTION

1. Field of the Invention

The present invention relates to a bioreactor for improved productivity of photosynthetic algae. More particularly, the invention is concerned with bioreactors and bioreactor systems for optical enhancement of photosynthetic productivity of algae.

2. Discussion of the Background

In the past decade, there has been considerable activity relating to production of photosynthetic microalgae for commercial purposes. Special industries aiming to produce health food, food additives, animal feed, biofertilizers and an assortment of natural products (most notably β-carotene) have been established. Recently, microalgae have been suggested as a means to sequester carbon from the industry, and hydrogen producing algae as a source of energy.

It is known that algae productivity is limited by three major factors: light, nutrients and temperature. Historically, most efforts have been invested in developing the optimum nutrients for any specific algae. This included means to saturate the photosynthetic system with $CO_2$. Still, temperature remains a major limiting factor in commercial, outdoor production. Optimal conditions for efficient production are usually selected in accordance with the climatic conditions prevailing in a chosen site. Yet, even in such sites, winter and night temperatures, as well as morning hour temperatures pose serious limitations to growth rates.

Under optimal temperature and nutrient conditions, the single most important factor in limiting productivity is light. In order to address this problem, open algae producing ponds are made as shallow as practically possible for improving the surface to volume ratio, and stirring is increased to reduce the time the algae stay in darkness, which, in concentrated cultures, is a few millimeters from the surface.

Attempts have also been made to grow algae in tubes, again increasing the surface to volume ratio and hence light conditions thereof. Conventional tubes, however, do not allow temperature control and the light is limited by ambient conditions. If light intensity is less than maximum and strong light attenuation with depth of culture occurs, limitations to photosynthetic activity are imposed.

Still further development has recently been made by growing algae in tubes in which special light guides (fiber optics) are inserted in the tubes. These fibers uniformly diffuse a large proportion of the light passing through them. A solar concentrator is used to concentrate solar light onto one end of the fibers. The fiber optics in this arrangement occupy a large proportion of the reactor's volume and a large proportion of the light is lost through the end of the fibers. Since the reactor itself is in the dark, the use of the solar concentrator results in very low light intensities per surface unit within the growth chamber. No temperature control is available in this system.

SUMMARY OF THE INVENTION

It is therefore a broad object of the present invention to ameliorate the disadvantage of the above-described known devices, and to provide a bioreactor in which the light regime therein is improved.

It is a further object of the present invention to provide a bioreactor in which the average light intensity reaching the algae is increased.

Still a further object of the present invention is to provide a bioreactor in which the spectral quality of the impinging light can be adjusted in accordance with specific requirements of an algae species which is produced.

Yet still a further object of the present invention is to provide a bioreactor in which the temperature prevailing inside the reactor can be adjusted and controlled.

In accordance with the present invention there is therefore provided a bioreactor for improved productivity of photosynthetic algae, comprising a tubular housing surrounding a tubular envelope located therein and defining a space therebetween to be filled with fluid, said housing and envelope being made of at least a translucent material, said housing and envelope having inlet and outlet ports providing access to said space and to the interior of said envelope, and means for mixing a algae media disposed inside said envelope.

The invention also provides a bioreactor system for improved productivity of photosynthetic algae, comprising a tubular housing surrounding a tubular envelope located therein and defining a space therebetween, said housing and envelope being made of at least a translucent material, said housing and envelope having inlet and outlet ports providing access to said space and the interior of said envelope, and means for mixing an algae media disposed inside said envelope, said envelope containing a fluid of selective refractive index, wherein, for a given geometrical relationship between said housing and envelope the radiation concentration power is controlled by modifying the refractive index of said fluid.

The invention will now be described in connection with certain preferred embodiments with reference to the following illustrative figures so that it may be more fully understood.

With specific reference now to the figures in detail, it is stressed that the particulars shown are by way of example and for purposes of illustrative discussion of the preferred embodiments of the present invention only and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

DESCRIPTION OF THE PREFERRED EMBODIMENT

Figure 1:
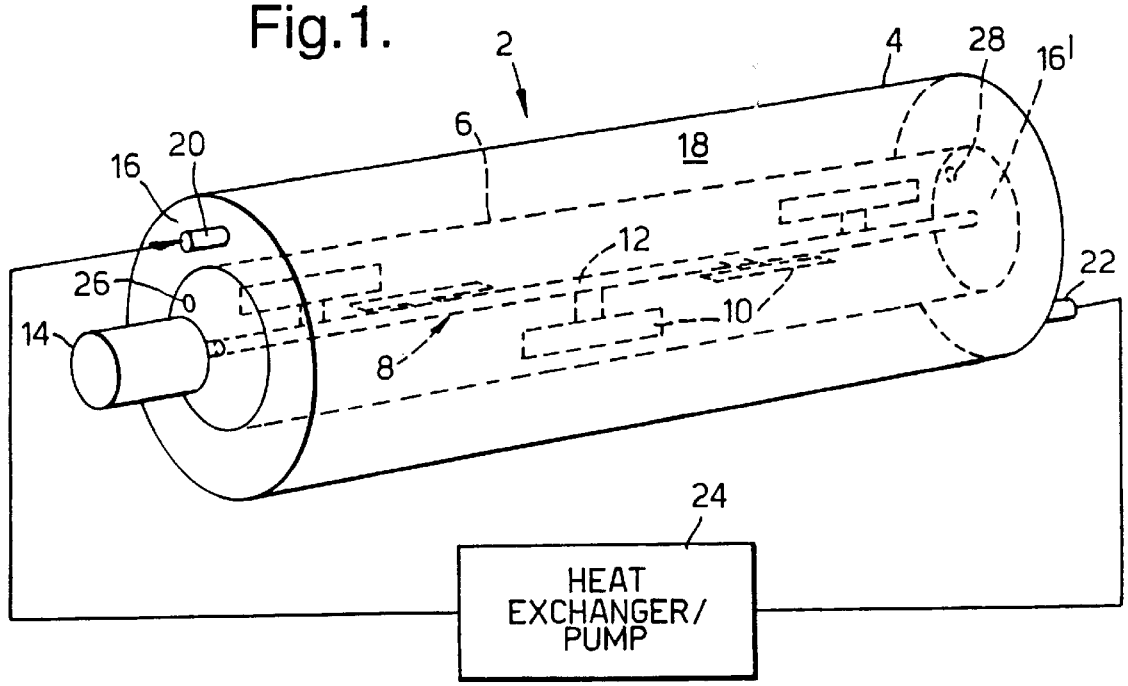
FIG. 1 is an isometric and schematic illustration of a bioreactor according to the present invention.

Referring to FIG. 1, there is shown a bioreactor 2, particularly a bioreactor for improving the productivity of photosynthetic algae by optical means. The bioreactor 2 includes an outer tubular housing 4, and an inner tubular envelope 6. Advantageously the housing 4 and the envelope 6 are cylindrical and coaxially disposed with respect to each other. Both the housing 4 and the envelope 6 are made of at least a translucent and preferably, of a transparent, material.

Inside the envelope 6 there are optionally provided mixing means 8, e.g., composed of a plurality of vanes 10 mounted on an axis 12 driven by a motor 14. Preferably the end portions of the housing 4 and the envelope 6 are connected to common bases or end walls 16, 16'.

As seen, the outer surface of the envelope 6 and the inner surface of housing 4 define thereinbetween a space 18 to be filled with fluid, the access to which space is effected via an inlet nozzle 20 and an outlet nozzle 22. The two nozzles 20 and 22 are in fluid communication through a heat exchanger/pump 24.

Access to and from the volume inside the envelope 6 is accomplished at one end wall thereof through an opening or a capillary port 26 and at the other end wall through an injector 28. Advantageously, the walls 16, 16' are dismountable to facilitate convenient access to the volume inside the housing and envelope for cleaning and other purposes.

The mixing of algae media introduced into the envelope 6 can be effected by other means than the mechanical mixer shown in FIG. 1. For example, since air is injected into the envelope for the purpose of flushing out gases accumulated therein, which air also carries $CO_2$ added thereto for the benefit of the algae, the stream of air can also be utilized for mixing the algae media. The air stream can be propelled through a duct replacing the axis 12, which duct is provided with small holes or is made of porous material through which small bubbles are emitted causing a mixing action. Still alternatively, mixing can be achieved by a pump (not shown), circulating the algae media via several bioreactors, inter-connected in series.

Figure 2:
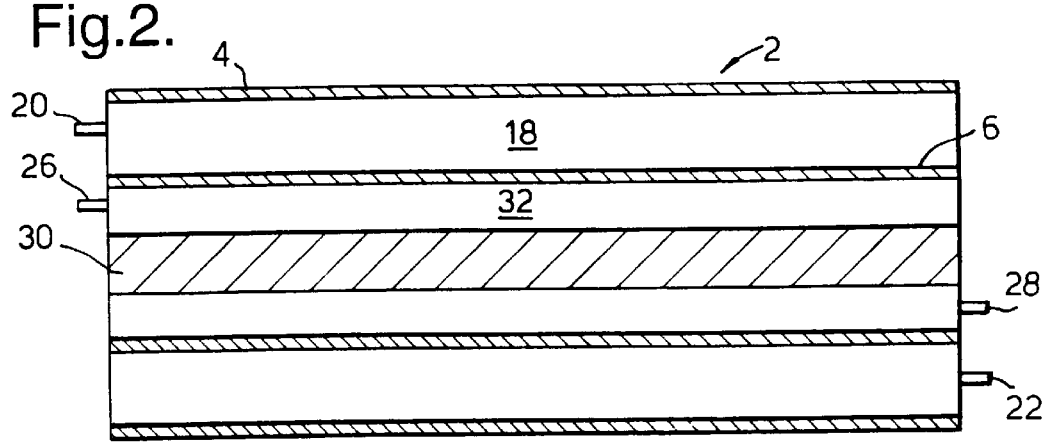
FIG. 2 is a cross-sectional view of a further embodiment of a bioreactor according to the present invention.

The bioreactor 2 can be scaled up by increasing the diameters of the housing 4 and envelope 6. As shown in FIG. 2, in order to maintain the algae solution at an optimal depth, there is inserted a rod 30 inside the envelope 6, so as to form an annular space 32 between the surface of the rod and the inside surface of the envelope. The surface of the rod 30 may be coated with material to provide reflection of the impinging radiation. Instead of a rod, there may be inserted a tube with or without a reflective coating. If the tube is transparent, there may not be a need for such coating.

Obviously, if the space 32 inside the envelope 6 is annular, the more suitable mixing means would be air bubbles or circulating means, as described above.

Figure 3:
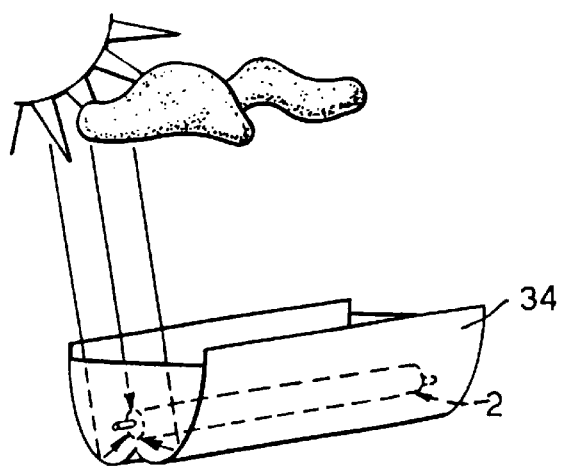
FIG. 3 is a schematic illustration of the bioreactor of FIG. 1 as utilized with a solar concentrator.

Referring to FIG. 3, there is seen the bioreactor 2 located in the center of a Compound Parabolic solar Concentrator (CPC) 34 so as to form a solar bioreactor of a higher degree of efficiency by providing additional solar radiation when required and by the superior distribution of light all around the bioreactor 2.

The arrangement of the housing 4, and envelope 6 encasing the materials used, which will be referred to in greater detail hereinafter, together with the properties of the external solution used in the volume enclosed between the envelope and the housing, and the internal algae media, serve as a solar concentrator for algae grown within the envelope 6. The concentration power is determined by the ratio of the diameters of the housing 4 and envelope 6 (in a case where both the housing and envelope are cylindrical), as well as by the refractive index of the materials used, which materials should be adjusted with respect to the selected diameters. Thus, the light concentration power of the bioreactor is set at a predetermined level. The external solution poured in the space 18, provides the means for spectral and temperature controls. The spectral quality of the solution can be modified by including therein color filters and/or fluorescence dyes. Two filters, e.g., rodamine or dicromite can be used in the solution, which filters modify the red to blue ratio of the light reaching the algae. The walls of the housing 4 and envelope 6, as well as the solution inside the space 18 also act as light filters, in effect removing substantially all of the UV and IR radiation. The same solution prevailing inside the space 18 is also utilized to control the temperatures of the algae inside the envelope 6 by circulating same through the heat exchanger/pump 24 at a controlled rate.

Nutrients are provided by the algae media itself, while $CO_2$ is supplied thereto by injecting same via the capillary port 26. The carbon supplied is controlled by a PH-stat controller (not shown) operated by a thin electrode inserted into the envelope 6 through port 26.

Experiments were conducted with a bioreactor 2, in accordance with the following example:

A solar bioreactor 2 was constructed of tubular housing 4 and envelope 6, both made of glass, having respective diameters of 5 and 7.5 cm (ratio of diameters 1.5). The refractive index of the external and internal media was adjusted to 1.5 by dissolving NaCl providing 1.5 times incident sunlight at the inner surface of the envelope (i.e., at the surface of the algae media). The maximal depth of the algae media was about 2.5 cm and it was efficiently mechanically stirred by a series of vanes 10 rotating at a speed of 16 revolutions per minutes, or alternatively, stirred by air bubbles. The bioreactor 2 was placed horizonally in parallel to the sun's daily track, or perpendicularly to the solar orbit. A dilute solution of Dunaliella bardawil algae was used as a model and was put in the envelope 6. Temperature in the external solution was adjusted to provide a constant temperature of 27–32° C. A similar reactor was placed inside a CPC 30 providing overall concentrating power at the surface of the algae media of about 4.

Samples of the algae media were taken daily through a septum and the algae were counted and β-carotene (the end product in this case) concentration was determined. The results were compared with maximum yields obtained in laboratory scale production, small scale outdoor ponds used for local production of β-carotene, and with maximal yields obtained in a large scale commercial open pond plant (Table 1).

It is important to note that the CPC results were obtained in the summer, when light intensities are maximal and a light stress effect is likely. The major advantage of the CPC is expected in the winter, as shown by the results obtained in the experiments conducted, which were substantially the same as in the summer time. Similar favourable results are also expected to take place in areas where light intensities are below the maximum sustained by the microalgae. It is also important to note that the results for the open ponds can only be obtained in the summer. During the winter, growth is strongly limited by low temperatures and dilution of the algae culture by rain water. Both of these effects are eliminated in the solar bioreactor, which was operated throughout the year.

TABLE 1

Yields of β-carotene in conventional ponds and the proposed solar bioreactor without and with a x3 CPC.

|  | β-Carotene (pg/cell) | Cell Number ($10^6$/ml) | Total β-Carotene Yield (pg/ml) |
|---|---|---|---|
| small ponds | 10 | 0.7 | 7 |
| corpmercial ponds | 15 | 0.3 | 5 |
| bioreactor I | 17 | 4.2 | 71 |

TABLE 1-continued

Yields of β-carotene in conventional ponds and the
proposed solar bioreactor without and with a x3 CPC.

|  | β-Carotene (pg/cell) | Cell Number ($10^6$/ml) | Total β-Carotene Yield (pg/ml) |
| --- | --- | --- | --- |
| bioreactor I + CPC | 12 | 4.0 | 48 |
| bioreactor II | 50 | 9.7 | 64 | where:
bioreactor I was oriented horizontally and contained mechanical mixing means, and
bioreactor II was oriented perpendicularly to solar orbit and contained air mixing means.

It will be evident to those skilled in the art that the invention is not limited to the details of the foregoing illustrated embodiments and that the present invention may be embodied in other specific forms without departing from the spirit or essential attributes thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. A bioreactor system for improved productivity of photosynthetic algae, comprising a tubular housing surrounding a tubular envelope located therein and defining a space therebetween, said housing and envelope being made of at least a translucent material, said housing and envelope having inlet and outlet ports providing access to said space and the interior of said envelope, and means for mixing an algae media disposed inside said envelope;
    said space containing a fluid having a refractive index selected with respect to a given geometrical relationship between said housing and envelope and said fluid is introducible into said space through the inlet and outlet ports; and
    most solar radiation impinging on said housing will reach the algae media and the light concentration power of the bioreactor is set at a predetermined level.

2. The bioreactor of claim 1, further comprising a heat exchanger in fluid communication with said space.

3. The bioreactor of claim 1, wherein said housing and said envelope are cylindrical.

4. The bioreactor of claim 1, wherein said housing and said envelope are cylindrical of predetermined ratio of diameters.

5. The bioreactor of claim 1, wherein said envelope defines an annular space.

6. The bioreactor of claim 1, wherein said tubular housing and envelope are commonly connected to end walls and said inlet and outlet ports are fitted in said end walls.

7. The bioreactor of claim 1, wherein said means for mixing comprises a plurality of vanes mounted on a common axis traversing the length of said envelope, the vanes being driven by a motor.

8. The bioreactor of claim 1, wherein said means for mixing comprises an air stream injected into said envelope.

9. The bioreactor of claim 1, wherein said means for mixing comprises a pump capable of circulating said algae media through a plurality of said housings and envelopes which are interconnected.

10. The bioreactor of claim 1, wherein said fluid comprises at least one member selected from the group consisting of color filters and fluorescent dyes for modifying the spectral quality of the light radiation reaching said envelope.

11. The bioreactor of claim 1, further comprising a solar concentrator for efficient reflection of solar radiation onto a surface area of said housing and envelope.

12. The bioreactor of claim 11, wherein said solar concentrator comprises means for controlling an angle of orientation thereof with respect to the sun's orbit.

13. The bioreactor of claim 1, wherein said envelope is provided with an injection capillary for controlling $CO_2$ concentrations in said algae media disposed in said envelope, by a PH-stat controller.

14. A bioreactor system for improved productivity of photosynthetic algae, comprising:
    a housing formed of a material selected from the group consisting of translucent and transparent materials;
    an envelope located in the housing such that a space is defined between the housing and the envelope, the envelope formed of a material selected from the group consisting of translucent and transparent materials;
    inlet and outlet ports provided in the housing and envelope, and providing access to the space and to an interior of the envelope;
    an algae media inside the envelope;
    a mixer for mixing the algae media;
    said space containing a fluid having a refractive index selected with respect to a given geometrical relationship between said housing and envelope and said fluid is introducible into said space through the inlet and outlet ports; and
    most solar radiation impinging on said housing will reach the algae media and the light concentration power of the bioreactor is set at a predetermined level.

15. The bioreactor of claim 14, wherein the mixer comprises a plurality of vanes mounted on a common axis traversing the length of the envelope, the vanes being driven by a motor.

16. The bioreactor of claim 14, wherein the mixer comprises an air stream injector.

17. The bioreactor of claim 14, wherein the mixer comprises a pump capable of circulating the algae media through a plurality of said housings and envelopes which are interconnected.

18. The bioreactor of claim 14, wherein the fluid comprises at least one member selected from the group consisting of color filters and fluorescent dyes for modifying the spectral quality of the light radiation reaching said envelope.

19. The bioreactor of claim 14, further comprising a solar concentrator for efficient reflection of solar radiation onto a surface area of the housing and envelope.

20. The bioreactor of claim 14 further comprising a heat exchanger in fluid communication with said space.

21. The bioreactor of claim 14, wherein the housing and the envelope are cylindrical.

22. The bioreactor of claim 14, wherein the envelope defines an annular space.

* * * * *